United States Patent

Brunner et al.

(10) Patent No.: US 8,105,668 B2
(45) Date of Patent: Jan. 31, 2012

(54) CRYSTALLINE FORM OF 2-(4,6-BIS-BIPHENYL-4-YL-1,3,5-TRIAZIN-2-YL)-5-(2-ETHYL-(N)-HEXYLOXY)PHENOL

(75) Inventors: Frédéric Brunner, Chézard (CH); Martin Von Büren, Muttenz (CH); Markus Grob, Reinach (CH); Daisuke Fujiki, Binningen (CH)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 12/744,717

(22) PCT Filed: Nov. 26, 2008

(86) PCT No.: PCT/EP2008/066208
§ 371 (c)(1),
(2), (4) Date: Oct. 15, 2010

(87) PCT Pub. No.: WO2009/071475
PCT Pub. Date: Jun. 11, 2009

(65) Prior Publication Data
US 2011/0027509 A1 Feb. 3, 2011

(30) Foreign Application Priority Data
Dec. 3, 2007 (EP) ..................... 07122095

(51) Int. Cl.
*B29D 22/00* (2006.01)
*B29D 23/00* (2006.01)
*B32B 1/08* (2006.01)
*B29C 65/00* (2006.01)

(52) U.S. Cl. ....... 428/35.5; 428/412; 428/480; 428/500; 544/216; 252/405; 524/100

(58) Field of Classification Search ............... 428/35.5, 428/412, 480, 500; 544/216; 252/405; 524/100
See application file for complete search history.

(56) References Cited

U.S. PATENT DOCUMENTS

| 6,060,543 A | 5/2000 | Bolle |
| 2002/0083641 A1 | 7/2002 | Leppard et al. |
| 2007/0054991 A1 | 3/2007 | Rudiger et al. |
| 2008/0146703 A1 | 6/2008 | Kliesch |
| 2009/0258978 A1 | 10/2009 | Ruediger et al. |

FOREIGN PATENT DOCUMENTS

| DE | 10135795 A1 | 4/2002 |
| EP | 1762591 A | 3/2007 |
| WO | 2007/088114 A | 8/2007 |
| WO | 2008/0107095 | 9/2008 |

*Primary Examiner* — Michael C Miggins
(74) *Attorney, Agent, or Firm* — Tyler A. Stevenson

(57) ABSTRACT

The crystalline form of 2-(4,6-bis-biphenyl-4-yl-1,3,5-triazin-2-yl)-5-(2-ethyl-(n)-hexyloxy)phenol, characterized by a X-ray diffraction pattern obtained by using Cu—Kα-radiation which exhibits the diffraction angles (2-Theta).

21 Claims, No Drawings

CRYSTALLINE FORM OF 2-(4,6-BIS-BIPHENYL-4-YL-1,3,5-TRIAZIN-2-YL)-5-(2-ETHYL-(N)-HEXYLOXY)PHENOL

The present invention relates to a new crystalline form of 2-(4,6-bis-biphenyl-4-yl-1,3,5-triazin-2-yl)-5-(2-ethyl-(n)-hexyloxy)phenol, the process for its preparation as well as a composition containing said crystalline form and the use of said crystalline form as UV absorber.

Particular hydroxyphenyl-triazines as stabilizers for organic polymers are for example described in U.S. Pat. No. 6,060,543, EP-A-1,762,591, DE-A-101 35 795, WO-A-2007/088,114, US-A-2008/0,146,703 and WO-A-2008/107,095.

It has been found that the specific crystal form of 2-(4,6-bis-biphenyl-4-yl-1,3,5-triazin-2-yl)-5-(2-ethyl-(n)-hexyloxy)phenol according to the present invention shows some advantages during processing in organic materials in comparison to the known 2-(4,6-bis-biphenyl-4-yl-1,3,5-triazin-2-yl)-5-(2-ethyl-(n)-hexyloxy)phenol product which is described in Example A8 of U.S. Pat. No. 6,060,543.

Besides the drying of the material, which can be performed at higher temperature, the dosing of the new crystal form in a hopper on an extruder has been improved. The crystal form already known in the art always tends to give lumps and is not so easy dosable. One of the reasons is the heat coming out of the feeder of the extruder heating up the dosing unit and leading to partial melting of the material at the walls of the hopper. Additionally, the material once fed into the extruder starts to melt later in the extruder barrel and therefore leading to a better transport in the barrel. The known form always tends to be already molten in the feeding zone leading to a "soup" with the polymer swimming in the UV absorber; this solid-liquid mixture is very difficult to transport out of the feeding zone into the extruder.

Particular advantages of the specific crystal form of 2-(4,6-bis-biphenyl-4-yl-1,3,5-triazin-2-yl)-5-(2-ethyl-(n)-hexyloxy)phenol according to the present invention are inter alia:
outstanding thermal stability;
improved storability, in particular under pressure;
improved processability of the polymer stabilized with said specific crystal form, in particular feedability, flowability and pneumatic transportability;
more consistant compounding with the polymer, which results to a more homogenous final stabilized polymer article;
more constant extrusion conditions during processing with the polymer are possible, which leads to less interruption of the production;
more constant melt strength of the molten polymer during processing;
more constant light performance of the polymer stabilized with said specific crystal form.

The present invention relates in particular to the crystalline form of 2-(4,6-bis-biphenyl-4-yl-1,3,5-triazin-2-yl)-5-(2-ethyl-(n)-hexyloxy)phenol, characterized by a X-ray diffraction pattern obtained by using Cu—Kα-radiation which exhibits the diffraction angles (2-Theta)

| 2-Theta | Counts per second |
| --- | --- |
| 3.49 | 137 |
| 6.67 | 5421 |
| 6.99 | 3946 |
| 7.41 | 2659 |
| 8.91 | 33 |
| 9.61 | 86 |
| 10.47 | 149 |
| 11.49 | 353 |
| 12.29 | 468 |
| 13.29 | 284 |
| 14.54 | 461 |
| 15.68 | 317 |
| 16.21 | 47 |
| 17.52 | 652 |
| 17.91 | 827 |
| 19.14 | 730 |
| 20.88 | 321 |
| 22.00 | 211 |
| 22.49 | 309 |
| 24.03 | 54 |
| 24.88 | 272 |
| 25.67 | 360 |
| 26.28 | 189 |

2-(4,6-bis-biphenyl-4-yl-1,3,5-triazin-2-yl)-5-(2-ethyl-(n)-hexyloxy)phenol has the following structural formula

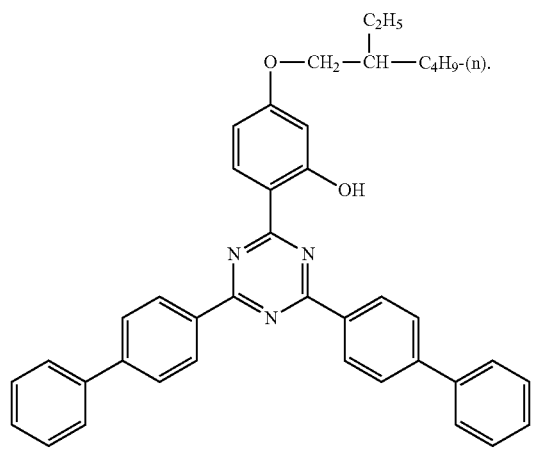

The present crystalline form of 2-(4,6-bis-biphenyl-4-yl-1,3,5-triazin-2-yl)-5-(2-ethyl-(n)-hexyloxy)phenol is in particular characterized by a melting range of 118-126° C., preferably with a peak maximum of 124° C., determined by Differential Scanning Calorimetry (DSC).

Another embodiment of the present invention is a process for the preparation of the present crystalline form of 2-(4,6-bis-biphenyl-4-yl-1,3,5-triazin-2-yl)-5-(2-ethyl-(n)-hexyloxy)phenol which comprises
reacting 4-(4,6-bis-biphenyl-4-yl-1,3,5-triazin-2-yl)-benzene-1,3-diol and 2-ethyl-(n)-hexylbromide in an aprotic polar organic solvent in the presence of a base;
removing the organic solvent and cooling the residual melt to a temperature of 80° C. to 130° C., preferably 100° C. to 110° C., in particular 110° C.;
adding a solvent (S) selected from the group consisting of linear or branched $C_4$-$C_{20}$alkane, the isomeric mixture thereof, $C_6$-$C_{12}$cycloalkane unsubstituted or substituted by 1 to 3 $C_1$-$C_8$alkyl, and the isomeric mixture thereof;
cooling the mixture to a temperature of 50° C. to 90° C., preferably 72° C.; washing with water to remove the salt formed during reaction; and
crystallizing 2-(4,6-bis-biphenyl-4-yl-1,3,5-triazin-2-yl)-5-(2-ethyl-(n)-hexyloxy)phenol from the organic phase; in particular by clarifying the organic phase through a filter;

and subsequently cooling to a final temperature of −20° C. to 50° C.; preferably 0° C.

Preferably, the molar ratio of 4-(4,6-bis-biphenyl-4-yl-1,3, 5-triazin-2-yl)-benzene-1,3-diol to 2-ethyl-(n)-hexylbromide is 1.0 to 0.3, preferably 0.6 to 0.65.

Examples of suitable aprotic polar organic solvents are dimethylformamide (DMF), dimethylacetamide (DMC), methyl cellosolve, ethyl cellosolve, organic ethers, in particular an aliphatic ether, and N-methylpyrrolidone. Dimethylformamide (DMF) is preferred.

Examples of the base are NaOH, NaHCO$_3$, Na$_2$CO$_3$, KOH, KHCO$_3$, K$_2$CO$_3$ and Na$_2$CO$_3$. K$_2$CO$_3$ is preferred.

It is advantageous to carry out the reaction at a temperature of 90° C. to 130° C., preferably 115° C.

The solvent (S) is preferably a linear or branched C$_7$-C$_{10}$alkane, in particular an isomeric mixture of heptane or an isomeric mixture of octane. Cyclohexane is also suitable. Particular suitable is further a hydrogenated petroleum fraction with boiling point starting from 50° C. till higher boiling point of 180° C.

A particular preferred process relates to a method wherein 4-(4,6-bis-biphenyl-4-yl-1,3,5-triazin-2-yl)-benzene-1,3-diol and 2-ethyl-(n)-hexylbromide are reacted in a molar ratio of 1.0 to 0.3, in particular 0.6, in 2-40% by mol, preferably 2 to 15% by mol or 8 to 12% by mol, in particular 10% by mol, of N,N-dimethylformamide, based on the mols of 4-(4,6-bis-biphenyl-4-yl-1,3,5-triazin-2-yl)-benzene-1,3-diol educt, in the presence of K$_2$CO$_3$ at a temperature of 80 to 140° C., preferably 100 to 120° C., in particular 115° C.; N,N-dimethylformamide is distilled off in vacuum and the reaction mixture is cooled to a temperature of 100 to 110° C.; 1 to 20% by mol of helptane isomeric mixture, based on the mols of 4-(4,6-bis-biphenyl-4-yl-1,3,5-triazin-2-yl)-benzene-1,3-diol educt, are added;

the reaction mixture is cooled to a temperature of 70 to 75° C. and washed with water to remove the salt formed during reaction;

the product 2-(4,6-bis-biphenyl-4-yl-1,3,5-triazin-2-yl)-5-(2-ethyl-(n)-hexyloxy)phenol is removed from the organic phase by clarifying the organic phase through a filter and subsequently cooling to a final temperature of −20° C. to 40° C., preferably −10° C. to 20° C. or −10° to 10° C., in particular 0° C.

For the intended use, the present crystal form can be in any desired geometrical product form of any desired particle size such as e.g. powder, flakes, pastilles, tablets, granules, etc.

The instant invention also relates to a stabilizer mixture containing the present crystalline form of 2-(4,6-bis-biphenyl-4-yl-1,3,5-triazin-2-yl)-5-(2-ethyl-(n)-hexyloxy)phenol and one or more of the following conventional additives for organic polymers, preferably in a weight ratio of e.g. 1:1000 to 1000 to 1; 1:100 to 100:1, 1:100 to 10:1 or 1:20 to 20:1, in particular 1:5 to 5:1.

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctyl-thiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxy-phenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis (3,5-di-tert-butyl-4-hydroxyphenyl) adipate.

1.4. Tocopherols, for example α-tocopherol, β-tocopherol, γ-tocopherol, δ-tocopherol and mixtures thereof (vitamin E).

1.5. Hydroxylated thiodiphenyl ethers, for example 2, 2'-thio-bis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butyl-phenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane.

1.7. O-, N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxy-benzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, di-dodecylmercaptoethyl-2,2-bis(3,5-di-tert-butyl-4-hydroxybenzyl)malonate, bis[4-(1,1,3,3-tetramethylbutyl) phenyl]-2,2-bis(3,5-di-tert-butyl-4-hydroxybenzyl) malonate.

1.9. Aromatic hydroxybenzyl compounds, for example 1,3, 5-tris(3,5-di-tert-butyl-4-hydroxy-benzyl)-2,4,6-trimethyl-benzene, 1,4-bis(3,5-di-tert-butyl-4-hydroxybenzyl)-2,3,5, 6-tetramethyl benzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxy-anilino)-1,3,5-triazine, 2-octylmercapto-4,6-bis(3,5-di-tert-butyl-4-hydroxyanilino)-1,3,5-tri-azine, 2-octylmercapto-4,6-bis(3,5-di-tertbutyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)iso-cyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylol-propane, 4-hydroxymethyl-1-phospha-2,6,7-trioxabicyclo[2.2.2]octane.

1.14. Esters of β-(5-tert-butyl-4-hydroxy-3-methylphenyl) propionic acid with mono- or poly-hydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3,5-dicyclohexyl-4-hydroxyphenyl)propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, tri-ethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of β-(3,5-di-tert-butyl-4-hydroxyphenyl)propionic acid e.g. N,N'-bis(3,5-di-tert-butyl-4-hydroxyphenylpropionyl)hexamethylenediamide, N,N'-bis(3,5-di-tert-butyl-4-hydroxy-phenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic Acid (Vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetra-methyl-4,4'-diaminodiphenylmethane, 1,2-bis[(2-methylphenyl)amino]ethane, 1,2-bis(phenyl-amino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenyl-amines, a mixture of mono- and dialkylated nonyldiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene.

2. UV Absorbers and Light Stabilizers 2.1. 2-(2'-Hydroxyphenyl)benzotriazoles, for example 2-(2'-hydroxy-5'-methylphenyl)-benzo-triazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethyl butyl)phenyl)benzotriazole, 2-(3',5'-di-tert-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyl-oxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-meth-oxycarbonylethyl)phenyl)benzotriazole, 2-(3'-tert-butyl-2'-hydroxy-5'-(2-octyloxycarbonyl-ethyl)phenyl)benzotriazole, 2-(3'-tert-butyl-5'-[2-(2-ethylhexyloxy)carbonylethyl]-2'-hydroxy-phenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylene-bis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]-benzotriazole; 2-[2'-hydroxy-3'-(1,1,3,3-tetramethylbutyl)-5'-(α,α-dimethylbenzyl)-phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butyl-phenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate, N-(β-carbomethoxy-β-cyanovinyl)-2-methylindoline, neopentyl tetra(α-cyano-β,β-di-phenylacrylate).

2.5. Nickel compounds, for example nickel complexes of 2,2'-thio-bis[4-(1,1,3,3-tetramethyl-butyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example carbonic acid bis(1-undecyloxy-2,2,6,6-tetramethyl-4-piperidyl)ester, bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-di-chloro-1,3,5-triazine, tris(2,2,6,6-tetramethyl-4-piperidyl) nitrilotriacetate, tetrakis(2,2,6,6-tetra-methyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyl-oxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylene-diamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino-1,2,2,6,6-pentamethylpiperidyl)-1,3,5-triazine and 1,2-bis(3-aminopropylamino) ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxo-spiro-[4,5]decane, a reaction product of 7,7,9,9-tetramethyl-2-cycloundecyl-1-oxa-3,8-diaza-4-oxo-spiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine, 2,4-bis[N-(1-cyclohexyloxy-2,2,6,6-tetramethylpiperidine-4-yl)-N-butylamino]-6-(2-hydroxyethyl)amino-1,3,5-triazine, 1-(2-hydroxy-2-methylpropoxy)-4-octadecanoyloxy-2,2,6,6-tetramethylpiperidine, 5-(2-ethylhexanoyl)oxymethyl-3,3,5-trimethyl-2-morpholinone, Sanduvor (Clariant; CAS Reg. No. 106917-31-1], 5-(2-ethylhexanoyl)oxymethyl-3,3,5-trimethyl-2-morpholinone, the reaction product of 2,4-bis[(1-cyclohexyloxy-2,2,6,6-piperidine-4-yl)butylamino]-6-chloro-s-triazine with N,N'-bis(3-aminopropyl)ethylenediamine), 1,3,5-tris(N-cyclohexyl-N-(2,2,6,6-tetramethylpiperazine-3-one-4-yl)amino)-s-triazine, 1,3,5-tris(N-cyclohexyl-N-(1,2,2,6,6-pentamethylpiperazine-3-one-4-yl)-amino)-s-triazine.

2.7. Oxamides, for example 4, 4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy)phenyl-4,6-diphenyl-1,3,5-triazine, 2-(2-hydro-oxy-4- methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy]phenyl}-4,6-bis(2,4-dimethylphenyl)-1,3,5-triazine, 2,4-bis(4-[2-ethylhexyloxy]-2-hydroxyphenyl)-6-(4-methoxyphenyl)-1,3,5-triazine, 2-[2-hydroxy-4-(1-(isooctyloxycarbonyl)ethoxy)phenyl]-4,6-diphenyl-1,3,5-triazine.

2.9. Quinoline derivatives such as e.g. the commercially available UVINUL® S-Pack.

2.10. Benzoxazinone derivatives such as e.g. the commercially available CYASORB® UV 3638.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyldihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-di-cumylphenyl)pentaerythritol diphosphite, bis(2,6-di-tert-butyl-4-methylphenyl)pentaerythritol diphosphite, diisodecyloxypentaerythritol diphosphite, bis(2,4-di-tert-butyl-6-methylphenyl)-pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos 168, Ciba Specialty Chemicals Inc.), tris(nonylphenyl) phosphite,

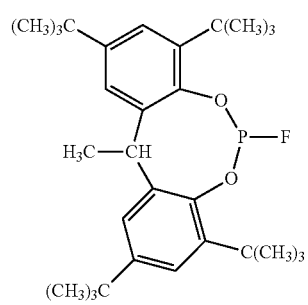

(A)

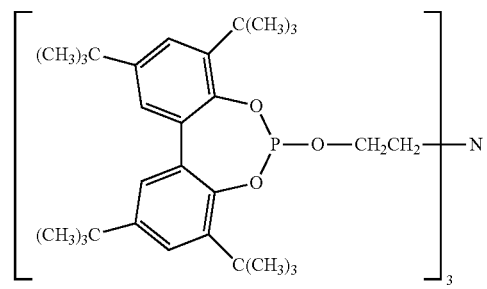

(B)

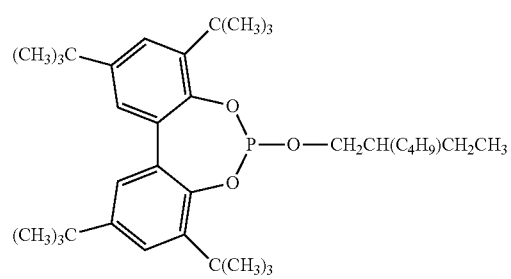

(C)

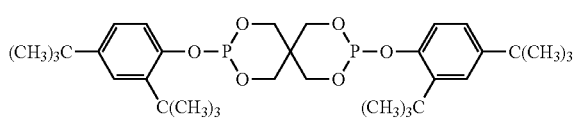

(D)

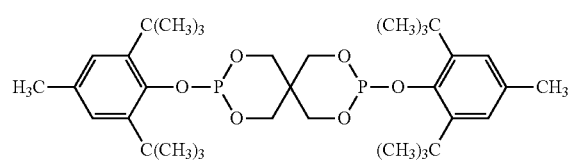

(E)

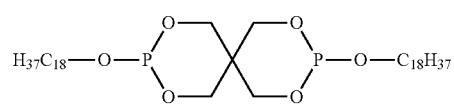

(F)

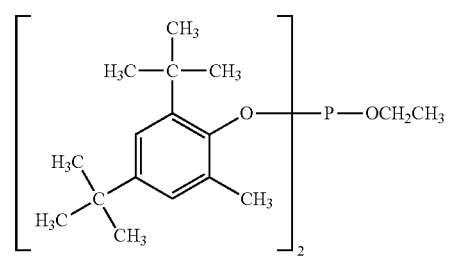

(G)

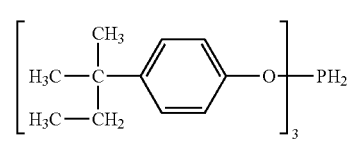

(H)

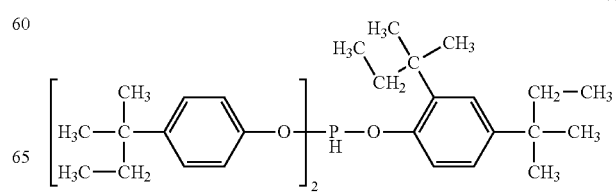

(I)

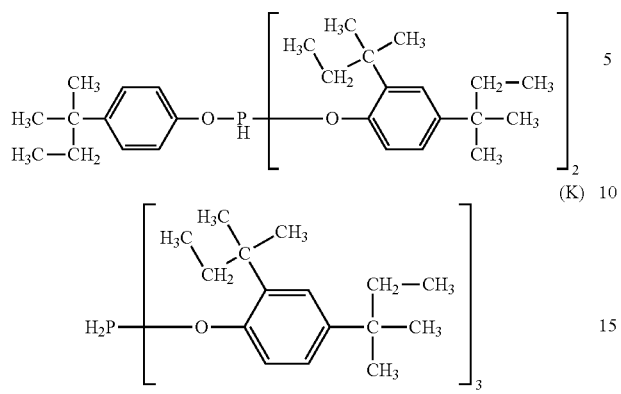

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenylnitrone, N-ethyl-alpha-methylnitrone, N-octyl-alpha-heptylnitrone, N-lauryl-alpha-undecylnitrone, N-tetradecyl-alpha-tridecylnnitrone, N-hexadecyl-alpha-pentadecylnitrone, N-octadecyl-alpha-heptadecylnitrone, N-hexadecyl-alpha-heptadecylnitrone, N-ocatadecyl-alpha-pentadecylnitrone, N-heptadecyl-alpha-hepta-decylnitrone, N-octadecyl-alpha-hexadecylnitrone, nitrone derived from N,N-dialkylhydroxylamine derived from hydrogenated tallow amine.

7. Thiosynergists, for example dilauryl thiodipropionate, dimistryl thiodipropionate, distearyl thiodipropionate or distearyl disulfide.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilizers, for example copper salts in combination with iodides and/or phosphorus compounds and salts of divalent manganese; stabilizers based on iron such as e.g. those described in US-A-2008/0,146,717, US-A-2008/0,146,718, EP-A-1,498,445 and WO-A-2005/007,727, in particular elementary iron or $Fe_2O_3$.

10. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyl-dibenzylidene)sorbitol, and 1,3:2,4-di(benzylidene)sorbitol.

12. Fillers and reinforcing agents, for example calcium carbonate, silicates, glass fibres, glass beads, asbestos, talc, kaolin, mica, barium sulfate, metal oxides and hydroxides, car-bon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839, EP-A-0591102; EP-A-1291384, US-A-2006/0,135,792 or 3-[4-(2-acetoxyethoxy)phenyl]-5,7-di-tert-butylbenzofuran-2-one, 5,7-di-tert-butyl-3-[4-(2-stearoyloxyethoxy)phenyl]benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one, 3-(2-acetyl-5-isooctylphenyl)-5-isooctylbenzofuran-2-one, 5,7-di-tert-butyl-3-(4-hydroxyphenyl)benzofuran-2-one, 5,7-di-tert-butyl-3-[4-(2-hydroxy-ethoxy)phenyl]benzofuran-2-one, 5,7-di-tert-butyl-3-[4-R*-phenyl]benzofuran-2-one with R* being a group

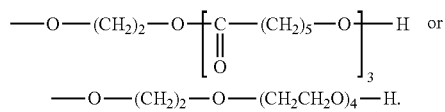

The conventional additive is preferably a sterically hindered amine compound containing a divalent group of the formula

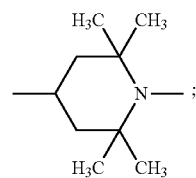

in particular one selected from item 2.6 of the above list.

According to a particularly preferred embodiment, the weight ratio of the present crystal form to the sterically hindered amine is for example 1000:1 to 1:1000 or 1:100 to 10:1, in particular 1:10 to 10:1.

A further UV absorber selected from items 2.1, 2.2 and 2.8 is also preferred as conventional additive. Cyanoacrylate based UV absorbers are also of interest as conventional additives.

Another conventional additive is a phosphate or phosphonite, in particular one of those described in item 4 of the above list.

A further embodiment of the present invention is a composition containing an organic material subject to degradation induced by light, heat or oxidation and the present crystalline form of 2-(4,6-bis-biphenyl-4-yl-1,3,5-triazin-2-yl)-5-(2-ethyl-hexyloxy)phenol.

Examples of a suitable organic material are:

1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultra-high molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).
   b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either $\pi$- or $\sigma$-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is gene-rated in-situ; propylene/butadiene copolymers, isobutylene/isoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$-$C_9$) including hydrogenated modifications thereof (e.g. tackifiers) and mixtures of polyalkylenes and starch.

Homopolymers and copolymers from 1.)-4.) may have any stereostructure including syndiotactic, isotactic, hemi-isotactic or atactic; where atactic polymers are preferred. Stereoblock polymers are also included.

5. Polystyrene, poly(p-methylstyrene), poly($\alpha$-methylstyrene).

6. Aromatic homopolymers and copolymers derived from vinyl aromatic monomers including styrene, $\alpha$-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or $\alpha$-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfo-chlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from $\alpha,\beta$-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitrile/vinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 10/10 or 12/12, polyamide 11, polyamide 12, aromatic polyamides starting from m-xylene diamine and adipic acid (e.g. Nylon MXD6); polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones or lactides, for example polyethylene terephthalate, polybutylene terephthalate, poly-1,4-dimethylolcyclohexane terephthalate, polyalkylene naphthalate and polyhydroxybenzoates as well as copolyether esters derived from hydroxyl-terminated polyethers, and also polyesters modified with polycarbonates or MBS. Copolyesters may comprise, for example—but are not limited to—polybutylensuccinate/terephtalate, polybutyleneadipate/terephthalate, polytetramethyleneadipate/terephthalate, polybutylensuccinate/adipate, polybutylensuccinate/carbonate, poly-3-hydroxybutyrate/octanoate copolymer, poly-3-hydroxybutyrate/hexanoate/decanoate terpolymer. Furthermore, aliphatic polyesters may comprise, for example—but are not limited to—the class of poly(hydroxyalkanoates), in particular, poly(propiolactone), poly(butyrolactone), poly(pivalolactone), poly(valerolactone) and poly(caprolactone), polyethylenesuccinate, polypropylenesuccinate, polybutylenesuccinate, polyhexamethylenesuccinate, polyethyleneadipate, polypropyleneadipate, polybutyleneadipate, polyhexamethyleneadipate, polyethyleneoxalate, polypropyleneoxalate, polybutyleneoxalate, polyhexamethyleneoxalate, polyethylenesebacate, polypropylenesebacate, polybutylenesebacate and polylactic acid (PLA) as well as corresponding polyesters modified with polycarbonates or MBS. The term "polylactic acid (PLA)" designates a homopolymer of preferably poly-L-lactide and any of its blends or alloys with other polymers; a co-polymer of lactic acid or lactide with other monomers, such as hydroxy-carboxylic acids, like for example, glycolic acid, 3-hydroxy-butyric acid, 4-hydroxy-butyric acid, 4-hydroxy-valeric acid, 5-hydroxy-valeric acid, 6-hydroxy-caproic acid and cyclic forms thereof; the terms "lactic acid" or "lactide" include L-lactic acid, D-lactic acid, mixtures and dimers thereof, i.e. L-lactide, D-lactide, meso-lacide and any mixtures thereof.

19. Polycarbonates and polyester carbonates.

20. Polyketones.

21. Polysulfones, polyether sulfones and polyether ketones.

22. Crosslinked polymers derived from aldehydes on the one hand and phenols, ureas and melamines on the other hand, such as phenol/formaldehyde resins, urea/formaldehyde resins and melamine/formaldehyde resins.

23. Drying and non-drying alkyd resins.

24. Unsaturated polyester resins derived from copolyesters of saturated and unsaturated dicarboxylic acids with polyhydric alcohols and vinyl compounds as crosslinking agents, and also halogen-containing modifications thereof of low flammability.

25. Crosslinkable acrylic resins derived from substituted acrylates, for example epoxy acrylates, urethane acrylates or polyester acrylates.

26. Alkyd resins, polyester resins and acrylate resins crosslinked with melamine resins, urea resins, isocyanates, isocyanurates, polyisocyanates or epoxy resins.

27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.

28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives; or poly-$\beta$-hydroxybutyrate.

29. Blends of the aforementioned polymers (polyblends), for example PP/EPDM, Poly-amide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA/HDPE, PA/PP, PA/PPO, PBT/PC/ABS, PBT/PET/PC or PPO/HIPS/PA.

30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.

31. Aqueous emulsions of natural or synthetic rubber, e.g. natural latex or latices of carboxylated styrene/butadiene copolymers.

The organic material is for example a synthetic polymer, preferably a translucent or transparent synthetic organic polymer, and can optionally be colored with colorants or pigments.

A suitable material is also e.g. a polyolefin, for example polyethylene, polypropylene or a copolymer of ethylene or propylene.

A preferred organic material is also an engineering plastic, e.g. acrylonitrile butadiene styrene (ABS), acrylic ester/styrene acrylonitrile copolymer (ASA), polymethyl methacrylate (PMMA), polycarbonate (PC), polyamide (PA), polybutylene terephthalate (PBT), polyethylene terephthalate (PET), polyethylene terephthalate glycol (PETG), polyphenylene oxide (PPO), polysulphone (PSU), polyethersulfone (PESU), polyetherketone (PEK), polyetheretherketone (PEEK) or polyimide.

One of the polymers indicated under items 13-19 of the above list is also of interest. Among those polymers preference is given to a polycarbonate, an acrylic polymer, a polyester, a polyamide, a polyacetal, a polyphenylene sulfide, in particular acrylics, a polyester or a polycarbonate.

Further preferred materials are
blends of polymethyl methacrylate (PMMA) and polyvinylidene flouride (PVDF),
ethylene vinyl acetate (EVA) films,
monoaxial oriented polypropylene (OPP) films,
biaxially oriented polypropylene (BOPP) films,
low density polyethylene (LDPE) articles,
linear low density polyethylene (LLDPE) articles,
high density polyethylene (HDPE) articles, and
polypropylene (PP) articles obtained by coextrusion.

Also preferred are coextruded polymethyl methacrylate (PMMA) laminates, in particular PMMA extruded over polyvinyl chloride (PVC), polycarbonate (PC), polyester or unsatured polyester resins.

Alloys in general can also be mentioned as preferred materials.

Another group of preferred materials are:
coextruded polycarbonate (PC) articles, in particular PC over polymethyl methacrylate copolymer or impact modified polymethyl methacrylate,
polymethyl methacrylate (PMMA) films and laminates,
polyethylene terephthalate (PET) films and coextruded sheets,
polyethylene terephthalate copolymer (PETG) films and sheets,
glycol modified polyester articles,
acrylate styrene acrylonitrile coextruded articles, in particular laminated films,
styrenics coextruded articles, in particular laminated films,
styrenic copolymer articles,
polyester articles,
polycarbonate articles,
cyclic olefin polymer (COP) articles,
triacetylcellulose (TAC) articles.

The amount of the present crystalline form and the amount of further conventional additives are determined by the nature of the substrate to be stabilized and by its intended end use. It is advantageous to employ e.g. 0.001-10%, preferably 0.01-5%, by weight of the present crystalline form and optionally the conventional additive, each, based on the material to be stabilized.

It is also possible to apply 0.0001 to 0.03% by weight, based on the material to be stabilized, of the present new crystalline form and 0.05 to 0.5% by weight, based on the material to be stabilized, of a different light stabilizer; e.g. one of those listed above under item 2.

Some additives, for example, fillers (e.g. glass fibers), flame retardants etc. may also be used in higher loadings, e.g. up to 60% or 50% by weight, especially up to 30% by weight of the polymer.

The present crystalline form or the present stabilizer mixtures can also be used in compositions comprising a binder for coatings, such as, for example, surface-coatings, or a photographic material.

The additives of the present stabilizer mixtures can be added to the material to be stabilized individually or as a mixture. If desired, the individual components can be mixed with one another before being incorporated into the polymer, for example in a dry state, by compacting or as a melt.

Incorporation of the present crystalline form and optionally one or more conventional additives into the polymer is carried out according to customary methods, such as, for example, dry mixing in powder form or wet mixing in the form of solutions, dispersions or suspensions, for example in inert solvents, water or oil. Incorporation of the present crystalline form and optionally one or more conventional additives can be carried out, for example, before or after shaping, or by applying or adding the dissolved or dispersed present crystalline form and optionally one or more conventional additives to the polymer material, with or without subsequent removal of the solvent or suspension agent/dispersant. Addition directly into the processing apparatus (e.g. extruder, mixer etc.), for example from a dry mixture or powder or as a solution or dispersion, suspension or melt, is possible.

The incorporation can be carried out in principle in any heatable vessel equipped with stirring apparatus, for example in closed apparatuses, such as kneaders, mixers or stirred vessels. Incorporation is preferably carried out in an extruder or kneader. The incorporation can be carried out under an inert atmosphere or equally in the presence of oxygen.

Any conventional apparatus for melting and mixing the polymer can be used for the addition of the present crystalline form and optionally one or more conventional additives. Suitable apparatuses, such as, for example, those mentioned above, are known in the art.

Preferably, the present crystalline form and optionally one or more conventional additives are added during the processing step in the extruder. Especially preferred processing apparatuses are single-screw extruders, twin-screw extruders running in opposite directions or in the same direction, planetary gear extruders or kneaders. Processing machines can be equipped with one or more degassing vessels to which a negative pressure can be applied.

Suitable extruders and kneaders are described, for example, in *Handbuch der Kunststoffextrusion, Vol.* 1 *Grundlagen,* editors F. Hensen, W. Knappe, H. Potente, 1989, pp. 3-7, ISBN: 3-446-14339-4 (*Vol.* 2 *Extrusionsanlagen* 1986, ISBN 3-446-14329-7).

The screw length may, for example, be 1-60, preferably 35-48, screw diameters. The rotation speed of the screw is preferably 10-600 revolutions per minute (rpm), especially 25-300 rpm.

The maximum throughput depends upon the screw diameter, the rotation speed and the driving force. The process according to the invention can also be operated at less than the maximum throughput by altering the mentioned parameters or by the use of metering machines.

When several components are added, these may be premixed or metered in individually.

The present crystalline form alone or optionally together with one or more conventional additives can be added to the polymer material also by spraying. Especially advantageous is addition of the present crystalline form alone or optionally together with one or more conventional additives by spraying during the deactivation of the polymerisation catalyst; in that case, the evolution of vapour can be utilised for deactivation. For example, addition by spraying, optionally together with other additives, can be advantageous in the case of spherically polymerised polyolefins.

The present crystalline form alone or optionally together with one or more conventional additives can be added to the polymer also in the form of concentrates (master batches) that comprise present crystalline form alone or optionally together with one or more conventional additives, for example, in a concentration of from 1 to 40%, preferably from 2 to 20%, relative to the weight of the polymer. That polymer does not necessarily have to have the same structure as the polymer to which the additives are finally added. The polymer may be used in the form of a powder, granules, solutions, suspensions or in the form of latices.

Incorporation can be carried out before or during shaping, or by applying the dissolved or dispersed present crystalline form alone or optionally together with one or more conventional additives to the polymer, where applicable with subsequent evaporation of the solvent. In the case of elastomers, these may also be stabilised in the form of latices. A further possibility of incorporating the present crystalline form alone or optionally together with one or more conventional additives into polymers comprises adding them before, during or immediately after polymerisation of the corresponding monomers or before crosslinking. The present crystalline form alone or optionally together with one or more conventional additives can be added as such or alternatively in encapsulated form (e.g. in waxes, oils or polymers).

The stabilised polymer compositions obtained in that manner can be converted into shaped articles, such as e.g. into fibres, films, monofilaments, tapes, non-woven fabrics, surface-coatings, monolithic sheets, multiwall sheets, panels, web panels, vessels, tubes and other profiles, by the usual methods, such as e.g. hot-pressing, spinning, thermoforming, extrusion, coextrusion, lamination, blow-moulding, rotomoulding, spraying or injection-moulding.

Examples of shaped articles are:

I-1) Floating devices, marine applications, pontoons, buoys, plastic lumber for decks, piers, boats, kayaks, oars, and beach reinforcements.

I-2) Automotive applications, in particular bumpers, dashboards, battery, rear and front linings, moldings parts under the hood, hat shelf, trunk linings, interior linings, air bag covers, electronic moldings for fittings (lights), panes for dashboards, headlamp glass, instrument panel, exterior linings, upholstery, automotive lights, head lights, parking lights, rear lights, stop lights, interior and exterior trims; door panels; gas tank; glazing front side; rear windows; seat backing, exterior panels, wire insulation, profile extrusion for sealing, cladding, pillar covers, chassis parts, exhaust systems, fuel filter/filler, fuel pumps, fuel tank, body side mouldings, convertible tops, exterior mirrors, exterior trim, fasteners/fixings, front end module, glass, hinges, lock systems, luggage/roof racks, pressed/stamped parts, seals, side impact protection, sound deadener/insulator and sunroof.

I-3) Road traffic devices, in particular sign postings, posts for road marking, car accessories, warning triangles, medical cases, helmets, tires.

I-4) Devices for plane, railway, motor car (car, motorbike) including furnishings.

I-5) Devices for space applications, in particular rockets and satellites, e.g. reentry shields.

I-6) Devices for architecture and design, mining applications, acoustic quietized systems, street refuges, and shelters.

II-1) Appliances, cases and coverings in general and electric/electronic devices (personal computer, telephone, portable phone, printer, television-sets, audio and video devices), flower pots, satellite TV bowl, and panel devices.

II-2) Jacketing for other materials such as steel or textiles.

II-3) Devices for the electronic industry, in particular insulation for plugs, especially computer plugs, cases for electric and electronic parts, printed boards, and materials for electronic data storage such as chips, check cards or credit cards.

II-4) Electric appliances, in particular washing machines, tumblers, ovens (microwave oven), dish-washers, mixers, and irons.

II-5) Covers for lights (e.g. street-lights, lamp-shades).

II-6) Applications in wire and cable (semi-conductor, insulation and cable-jacketing).

II-7) Foils for condensers, refrigerators, heating devices, air conditioners, encapsulating of electronics, semi-conductors, coffee machines, and vacuum cleaners.

III-1) Technical articles such as cogwheel (gear), slide fittings, spacers, screws, bolts, handles, and knobs.

III-2) Rotor blades, ventilators and windmill vanes, solar devices, swimming pools, swimming pool covers, pool liners, pond liners, closets, wardrobes, dividing walls, slat walls, folding walls, roofs, shutters (e.g. roller shutters), fittings, connections between pipes, sleeves, and conveyor belts.

III-3) Sanitary articles, in particular shower cubicles, lavatory seats, covers, and sinks.

III-4) Hygienic articles, in particular diapers (babies, adult incontinence), feminine hygiene articles, shower curtains, brushes, mats, tubs, mobile toilets, tooth brushes, and bed pans.

III-5) Pipes (cross-linked or not) for water, waste water and chemicals, pipes for wire and cable protection, pipes for gas, oil and sewage, guttering, down pipes, and drainage systems.

III-6) Profiles of any geometry (window panes) and siding.

III-7) Glass substitutes, in particular extruded plates, glazing for buildings (monolithic, twin or multiwall), aircraft, schools, extruded sheets, window film for architectural glazing, train, transportation, sanitary articles, and greenhouse. Plates and sheets can be used e.g. for verandas, leight weight roofs or as protection for windows against storm or hurricanes or as protection against avalanches.

III-8) Plates (walls, cutting board), extrusion-coating (photographic paper, tetrapack and pipe coating), silos, wood substitute, plastic lumber, wood composites, walls, surfaces, furniture, decorative foil, floor coverings (interior and exterior applications), flooring, duck boards, and tiles.

III-9) Intake and outlet manifolds.

III-10) Cement-, concrete-, composite-applications and covers, siding and cladding, hand rails, banisters, kitchen work tops, roofing, roofing sheets, tiles, and tarpaulins.

IV-1) Plates (walls and cutting board), trays, artificial grass, astroturf, artificial covering for stadium rings (athletics), artificial floor for stadium rings (athletics), and tapes.

IV-2) Woven fabrics continuous and staple, fibers (carpets/hygienic articles/geotextiles/monofilaments; filters; wipes/curtains (shades)/medical applications), bulk fibers (applications such as gown/protection clothes), nets, ropes, cables, strings, cords, threads, safety seat-belts, clothes, underwear, gloves; boots; rubber boots, intimate apparel, garments, swimwear, sportswear, umbrellas (parasol, sunshade), parachutes, paraglides, sails, "balloon-silk", camping articles, tents, airbeds, sun beds, bulk bags, and bags.

IV-3) Membranes, insulation, covers and seals for roofs, tunnels, dumps, ponds, dumps, walls roofing membranes, geomembranes, swimming pools, curtains (shades)/sunshields, awnings, canopies, wallpaper, food packing and wrapping (flexible and solid), medical packaging (flexible & solid), airbags/safety belts, arm- and head rests, carpets, centre console, dashboard, cockpits, door, overhead console module, door trim, headliners, interior lighting, interior mirrors, parcel shelf, rear luggage cover, seats, steering column, steering wheel, textiles, and trunk trim.

V) Films (packaging, dump, laminating, agriculture and horticulture, greenhouse, mulch, tunnel, silage), bale wrap, swimming pools, waste bags, wallpaper, stretch film, raffia, desalination film, batteries, and connectors.

VI-1) Food packing and wrapping (flexible and solid), BOPP, BOPET, bottles.

VI-2) Storage systems such as boxes (crates), luggage, chest, household boxes, pallets, shelves, tracks, screw boxes, packs, and cans.

VI-3) Cartridges, syringes, medical applications, containers for any transportation, waste baskets and waste bins, waste bags, bins, dust bins, bin liners, wheely bins, container in general, tanks for water/used water/chemistry/gas/oil/gasoline/diesel; tank liners, boxes, crates, battery cases, troughs, medical devices such as piston, ophthalmic applications, diagnostic devices, and packing for pharmaceuticals blister.

VII-1) Extrusion coating (photo paper, tetrapack, pipe coating), household articles of any kind (e.g. appliances, thermos bottle/clothes hanger), fastening systems such as plugs, wire and cable clamps, zippers, closures, locks, and snap-closures.

VII-2) Support devices, articles for the leisure time such as sports and fitness devices, gymnastics mats, ski-boots, inline-skates, skis, big foot, athletic surfaces (e.g. tennis grounds); screw tops, tops and stoppers for bottles, and cans.

VII-3) Furniture in general, such as desks, shelfs, etc., lamination, e.g. decorative foils, foamed articles (cushions, impact absorbers), foams, sponges, dish clothes, mats, garden chairs, stadium seats, tables, couches, toys, building kits (boards/figures/balls), playhouses, slides and play vehicles.

VII-4) Materials for optical and magnetic data storage.

VII-5) Kitchen ware (eating, drinking, cooking, storing).

VII-6) Boxes for CD's, cassettes and video tapes; DVD electronic articles, office supplies of any kind (ball-point pens, stamps and ink-pads, mouse, shelves, tracks), bottles of any volume and content (drinks, detergents, cosmetics including perfumes), and adhesive tapes.

VII-7) Footwear (shoes/shoe-soles), insoles, spats, adhesives, structural adhesives, food boxes (fruit, vegetables, meat, fish), synthetic paper, labels for bottles, couches, artificial joints (human), printing plates (flexographic), printed circuit boards, and display technologies.

VII-8) Devices of filled polymers (talc, chalk, china clay (kaolin), wollastonite, pigments, carbon black, $TiO_2$, mica, nanocomposites, dolomite, silicates, glass, asbestos).

VIII-1) Construction articles such as e.g. walls, material for tunnels etc.

Use in multilayer systems is also of interest. In this case, a polymer composition according to the invention having a relatively high content of present crystalline form alone or optionally together with one or more conventional additives, for example 5-15% by weight, is applied in a thin layer (10-100 µm) to a shaped article made from a polymer containing little or no present crystalline form. Application can be carried out simultaneously with the shaping of the basic body, e.g. by so-called coextrusion. Application can also be carried out, however, to the ready-shaped basic body, e.g. by lamination with a film or by coating with a solution. The outer layer or layers of the finished article have the function of an UV filter which protects the interior of the article from UV light. The outer layer contains preferably 5-15% by weight, especially 5-10% by weight, of the present crystalline form alone or optionally together with one or more conventional additives. In the case of transparent filter layers, the UV absorber can also be present in a different layer or in the single polymer layer.

The materials stabilised in that manner are distinguished by high resistance to weathering, especially by high resistance to UV light. As a result, the polymers retain their mechanical properties and also their colour and gloss for a long time even when used outside.

By using the present crystalline form alone or optionally together with one or more conventional additives in UV filter layers the passage of UV radiation and its associated damaging effects can be effectively prevented. It is therefore possible to produce inter alia protective containers or packaging films, for example for foodstuffs, medicaments or cosmetics.

The present crystalline form alone or optionally together with one or more conventional additives can advantageously be used in plastics films, for example polyethylene films, of the kind used in agriculture especially as a covering for hothouses. A particular advantage of hothouse films or agrofilms stabilized according to the invention is that it is possible to filter out the portion of UV radiation that directly damages the crops and/or that favours the spread of a number of pathogenic microorganisms, such as fungi and viruses, and pathogenic insects, such as e.g. whitefly, aphids, thrips etc. Those pests can be significantly reduced if the admission of UV radiation to the plants is prevented or reduced. [R. Reuveni et al., Plasticulture No. 102, p. 7 (1994); Y. Antignus et al., CIPA Congress March 1997, pp. 23-33]. Surprisingly, despite that UV filter action, the activity of useful insects in the hothouses (usually bumble-bees or bees), which require UV radiation in a specific bandwidth, is not disturbed. At the same time, the hydroxyphenyl UV absorbers of the present invention exhibit good compatibility and persistence in the polyolefin. The present invention accordingly also contributes to the improvement of agrofilms and describes a method for suppressing microbial infestation of cultivated plants, such as, for example, tomatoes, cucumbers, gourds, melons, citrus fruit, roses, strawberries, grapes, paprika etc.

Likewise of particular interest is a use of the present crystalline form alone or optionally together with one or more conventional additives as stabilizers for coatings and recording materials such as e.g. described in US-A-2006/0,252,857, paragraphs [0199] to [0306] for a similar UV stabilizer (system). US-A-2006/0,252,857 is incorporated herein by reference.

The present crystalline form is particularly effective in stabilizing thin mono- or multilayer films of a total thickness of e.g. 5 to 2000 µm, preferably 5 to 500 µm, in particular 20 to 500 µm. The multi-layers films may contain e.g. 2 to 10, preferably 2 to 7, in particular 2 to 5 layers. The layers can be made of identical or different polymers.

Laminates over glass, metal, paper, concrete or wood relate to a further preferred embodiment of the present invention.

Thus, mono- or multilayer polyester films stabilized with the specific crystal form of the UV absorber according to the present invention relate to a further particular preferred embodiment. Suitable films are for example described in US-A-2008/0,146,703, the disclosure of which is incorporated by reference herein. In more detail, in a multilayers polyester film containing a base layer B, the polymer of the base layer B and the remaining layers of the film (without taking into consideration UV stabilizers and other additives mentioned hereafter) preferably comprise at least 80% by weight thermoplastic polyester.

Weight percentages mentioned in the following refer to the mass of the respective layer comprising the respective compound.

Suitable polyesters comprise, amongst others, e.g. those made from ethylene glycol and terephthalic acid (=polyethylene terephthalate, PET), from ethylene glycol and naphthalene-2,6-dicarboxylic acid (=polyethylene-2,6-naphthalate, PEN), from 1,4-bishydroxymethylcyclohexane and terephthalic acid [=poly(1,4-cyclohexane dimethylene terephthalate), PCDT], and also from ethylene glycol, naphthalene-2,6-dicarboxylic acid and biphenyl-4,4'-dicarboxylic acid (=polyethylene 2,6-naphthalate bibenzoate, PENBB) and polyesters made from isophthalic acid and ethylene glycol, and also from any mixtures of said carboxylic acids and diols. Particularly preferred are polyesters made from at least 90 mol %, in particular from at least 95 mol % of ethylene glycol units and terephthalic acid units or of ethylene glycol units and naphthalene-2,6-dicarboxylic acid units. The remaining monomer units are e.g. derived from other aliphatic, cycloaliphatic, or aromatic diols and/or dicarboxylic acids.

Suitable other aliphatic diols are e.g. diethylene glycol, triethylene glycol, and aliphatic glycols according to the generic formula $HO-(CH_2)_n-OH$, wherein n is 1 to preferably less than 10.

Additionally the film polymer may contain up to 20% by weight of other polymers such as polyolefins (e.g. cycloolefin polymers, polypropylene etc.), polyamides or polyetherimides. Preferably their amount is less than 10% by weight, and particularly preferably the polymer consists of 100% by weight of the aforementioned polyesters.

The film may additionally contain common additives known to those skilled in the art; such as those listed above under items 1 to 14. Antiblocking agents are preferably used in the outer layers (layers A and C) of multi-layer films (ABC, B=base layer). Preferred examples of stabilizers used are phosphorus compounds, such as phosphoric acid or phosphoric acid esters. Further preferred examples of additives are radical scavengers and/or thermo stabilizers (e.g. those of the IRGANOX® range, preferably IRGANOX 1010®).

Typical antiblocking agents are inorganic and/or organic particles, e.g. calcium carbonate, crystalline or amorphous silica ($SiO_2$), talc, magnesium carbonate, barium carbonate, calcium sulfate, barium sulfate, lithium phosphate, calcium phosphate, magnesium phosphate, aluminum oxide, aluminum silicate, lithium fluoride, the calcium, barium, zinc, or manganese salts of the dicarboxylic acids used, titanium dioxide, kaolin, or crosslinked polystyrene particles, PMMA particles or acrylate particles.

Other antiblocking agents that can be used are mixtures of two or more different antiblocking agents or mixtures of antiblocking agents of the same composition but of different particle size. The antiblocking agents can be added to the individual layers in the respective advantageous amounts, e.g. in the form of a glycolic dispersion during polycondensation or by way of masterbatches during extrusion. Typically the amounts of antiblocking agents do not exceed 5% by weight, preferably not 1% by weight and those of the white pigments such as $TiO_2$ do not exceed 20% by weight.

According to the invention the total thickness of the polyester film is preferably 1 to 500 µm, particularly 10 to 50 µm, and especially 12 to 30 µm.

The film has one or more layers, across which all of the above additives can be included independently from each other. In multilayer films it has proven to be advantageous when the outer, light exposed layer (or in case of double sided light exposure and at least three-layered films, both outer layers) contain(s) more UV stabilizer than the inner layer/layers.

Economically and technically particularly advantageous embodiments are films with more than two layers in which more than 25%, preferably more than 30% and particularly preferably more than 35% of the UV stabilizer is contained in the outer layer(s), and particularly preferably one outer layer contains more than 25%, preferably more than 30% and particularly preferably more than 35% of the stabilizer.

For this particular use, it has proven advantageous, when the amount of UV stabilizer in each layer does not exceed 7% by weight, preferably when each layer does not contain more than 5% by weight UV stabilizer, since the stretch induced increase in crystallinity lowers the solubility of the UV stabilizer in the polyester matrix which may lead to exudation of UV stabilizer. Here the specific crystal form according to the present invention has proven to be particularly advantageous, because it may react with the polyester matrix and forms covalent bonds and exhibits a particularly low migration.

In multilayer embodiments it has proven advantageous, when at least the first two layers facing the incident light contain UV stabilizer. Preferably the amount of UV stabilizer in both of these two layers should not be lower than 0.1% by weight. In transparent embodiments (transparency>50%) it has proven advantageous when all layers of the film contain at least 0.1% by weight of UV stabilizer.

When the light facing layer of the film contains less than 4% by weight of white pigment (e.g. $TiO_2$, $BaSO_4$, $CaCO_3$ etc.) with an average particle size $d_{50}$ of greater than 200 nm, it has proven advantageous, when the outer layer contains at least 0.75% by weight UV stabilizer and particularly preferably at least 1.0% by weight of UV stabilizer.

In a preferred embodiment the film exhibits a longitudinal and transversal shrinkage of less than 10% at 200° C., preferably of less than 6% and particularly preferably of less than 4%. Further, at 100° C. the film exhibits an expansion of less than 3%, preferably of less than 1% and particularly preferably of less than 0.3%. This dimensional stability can be achieved e.g. by appropriate relaxation of the film prior to winding up.

In another preferred embodiment the film also exhibits an elastic modulus of greater than 3000 $N/mm^2$, preferably of greater than 3500 $N/mm^2$ and particularly preferably greater than 4100 $N/mm^2$ in the longitudinal and transversal directions. The F5 parameters (force at 5% elongation) in the longitudinal and transversal directions preferably are in the range of greater than 80 $N/mm^2$ and in particular greater than 90 $N/mm^2$. These mechanical properties can be obtained e.g. through appropriate biaxial stretching of the film according to methods well known to those skilled in the art.

Said shrink and mechanical properties favorably influence the film durability under UV aging and other weather conditions such as heat and moisture.

In a further preferred embodiment the film is coated on at least one side with an adhesion agent for print colors. Suitable coatings are e.g. acrylates or copolyesters with a sulfoisophthalic acid content of greater than 0.2% by weight.

The polyester matrix polymers of the respective layers are obtained for example by polycondensation, either starting from dicarboxylic acids and ethylene glycol (so called "PTA" process), or starting from the esters of dicarboxylic acids, preferably dimethyl esters and ethylene glycol (so called "DMT" process). Usable polyethylene terephthalates preferably have SV (solution viscosity) values in the range of from 600 to 900, and polyethylene-2,6-naphthalate from around 500 to 800.

Particles—if present—can already be added during the manufacture of the polyesters, if desired. For this purpose the particles are dispersed in ethylene glycol, optionally ground, decanted etc. and added to the reactor either in the (trans) esterification or polycondensation step. In a preferred alternative a concentrated polyester masterbatch containing particles or additives is prepared with a twin-screw-extruder and during film extrusion diluted with particle-free polyester. Further it is possible to add particles and additives directly to a twin-screw-extruder during film extrusion.

Non-cross-linked organic particles are e.g. either processed in a twin-screw-extruder to prepare a masterbatch, or are added directly during film extrusion.

The UV stabilizers can also be added to the film via the masterbatch technology. For this purpose a polyester raw material is plastified in a twin-screw-extruder and the UV stabilizer is added. Subsequently the mixture is extruded through an orifice into a water bath and quenched and granulated. It has proven advantageous when the masterbatch contains UV stabilizer in an amount from 1 to 33% by weight, preferably from 5 to 25% by weight and particularly preferably from 10 to 20% by weight. Amounts below this range are rather uneconomical and above 25% by weight the bonding of the UV stabilizer in the polymer matrix becomes insufficient, which at values above 33% by weight causes noticeable "exudation".

The UV stabilizers can also be added directly during film production. For this purpose respective amounts of stabilizer are dosed directly into the extruder. However, this yields in particular good distribution results when multi-(at least two)-screw-extruders are used.

Further it has proven advantageous, when the extruder intake is covered with a layer of inert gas (e.g. nitrogen or argon), because in direct extrusion at the film manufacturing equipment as well as in masterbatch production the UV stabilizer according to the invention may be sensitive toward oxidative stress caused by the high extrusion temperatures.

When single-screw-extruders are being used it has proven advantageous to pre-dry the polyesters. In case of twin-screw-extruders with a degassing zone the drying step can be omitted.

First, the polymer or polymer mixture of the layer, or in case of multilayer films of the individual layers are conveniently compressed and plastified in extruders. Then the melt(s) may be formed into flat film melts via a single- or multilayer nozzle, pressed through a slit die (wide slit nozzle) and drawn off via a chill roll and one or more take-up rolls, causing the film to cool down and solidify.

The film according to the invention is biaxially oriented, i.e. biaxially stretched. The biaxial stretching of the film is generally carried out sequentially. It is preferable to first orient longitudinally (i.e. in machine direction=MD direction) and then to orient transversely (i.e. perpendicularly to machine direction=TD direction). Longitudinal stretching can be carried out e.g. with the aid of two rolls running at different speeds corresponding to the desired stretching ratio. For transverse stretching, an appropriate tenter frame is generally used.

Instead of sequential stretching simultaneous stretching is possible but not necessarily required.

The temperature at which the stretching is carried out, can vary over a relatively wide range and depends on the desired properties of the film. In general the longitudinal stretching is carried out in a temperature range from e.g. 80 to 130° C. (heating-up temperature from 80 to 130° C.) and in transversal direction in a temperature range from e.g. 90° C. (start of stretching) to 140° C. (end of stretching). The ratio of longitudinal stretching is in the range from e.g. 2.0:1 to 5.5:1, preferably from 2.2:1 to 5.0:1. The ratio of transversal stretching is in general in the range from e.g. 2.4:1 to 5.0:1, preferably from 2.6:1 to 4.5:1.

In order to obtain the desired film properties it has proven advantageous, when the stretching temperature (MD and TD directions) is below 125° C. and preferably below 118° C.

Prior to transverse stretching, one or both surfaces of the film can be in-line coated by known processes. In-line coating can by way of example result in improved adhesion of a metal layer or printing ink, or else for improvement of antistatic performance or of processing performance. When the outer co-extruded layer does not contain particles for improvement of slip and winding characteristics, a particle containing coating can be applied at this stage.

During the subsequent heat setting the film is maintained under tension for a time period of about e.g. 0.1 to 10 s at a temperature of e.g. 150 to 250° C. and in order to obtain the preferred shrink value, relaxed in transversal direction by at least 1%, preferably by at least 3% and particularly preferably by at least 4%. The relaxation is preferably carried out in a temperature range from 150 to 190° C. Preferably less than 25% and greater than 5% of the total relaxation occurs within the first 25% of the relaxation time. The film is then conventionally wound up.

During film production it is conveniently ensured that reclaimed material can be reintroduced to the extrusion process in an amount of 20 to 60% by weight relative to the total weight of the film, without any significant adverse effect on the physical and optical properties of the film.

The film exhibits a very good UV stability, low intrinsic color, reduced content of UV stabilizer and reduced odor nuisance during film manufacture. Further it has been shown that due to the possible lower amount of the UV stabilizer the die-pressure variation, which occurs during film manufacture when switching back and forth between UV stabilized and non-stabilized film types, can be reduced such that fewer film breaks are observed upon switch-over.

Thus, the present invention also relates in particular to the following embodiments:

I) An article made of a composition according to the present invention.

II) An article as described above which is a molding, rotomolded article, injection molded article, blow molded article, film, tape, mono-filament, fiber, non-woven, profile, adhesive, putty or surface coating.

III) An article as described above which is an agricultural article.

IV) An article as described above which is an agricultural article selected from the group consisting of mulch films, small tunnel films, banana bags, direct covers, non-woven, twines and pots.

V) An article as described above which is a film, panel or multilayer sandwich panel and wherein the organic material is a polycarbonate.

Further preferred applications are transparent glazing applications, for example: biaxially oriented polyethylene terephthalate (BOPET) films, polymethyl methacrylate (PMMA) sheets, coextruded polycarbonate (PC) sheets, laminated PC sheets (laminate can be PMMA or other acrylic), coextruded polyethylene terephthalate (PET) or PET-G sheet or laminated PET or PET-G sheet, other lamination applications like BOPET on unsaturated polyester (UP) sheets, PMMA on polyvinyl chloride (PVC), PMMA or acrylic ester/styrene acrylonitrile copolymer (ASA) on polyolefinics sheets or on (wood polymer composites) WPC sheets, PMMA coextruded with PMMA etc.

Another embodiment of the present invention relates to a method for stabilizing an organic material against degradation induced by light, heat and oxidation, which comprises incorporating therein the present crystalline form.

Still another embodiment of the invention is the use of the present specific crystal form of 2-(4,6-bis-biphenyl-4-yl-1,3,5-triazin-2-yl)-5-(2-ethyl-(n)-hexyloxy)phenol as haze reducing agent; in particular a method for improving the haze of a polycarbonate, which comprises incorporating therein the present crystalline form.

The examples below illustrates the invention in greater detail. All percentages and parts mentioned in the present application are by weight, unless stated otherwise.

EXAMPLE A

Synthesis of 2-(4,6-bis-biphenyl-4-yl-1,3,5-triazin-2-yl)-5-(2-ethyl-(n)-hexyloxy)phenol using heptane isomeric mixture 300 g of N,N-dimethylformamide (DMF), 197.4 g of 4-(4,6-bis-biphenyl-4-yl-1,3,5-triazin-2-yl)-benzene-1,3-diol and 70 g of potassium carbonate are charged into a glass reactor. The mixture is heated to T=90° C. and 120 g of 2-ethyl-(n)-hexylbromide are added. After 4 hours reaction to 115° C., DMF is distilled off under vacuum at a temperature of 120° to 150° C. The residual product melt is cooled to 110° C. and 800 g of heptane isomeric mixture are added to the hot mixture. The heptane mixture is cooled at 72° C. and 200 g of water are added. After the first phase separation, several water washes are repeated till the last separated aqueous layer contains no salt any more. The residual water is removed by distillation and the heptane solution is clarified through a filter paper. The product is let to crystallize on cooling to a final temperature of 0° C. After filtration, the product is dried under vacuum at 100° C.

Yield: 230 g (95% of the theory)

Melting point (DSC): 118-126° C. (peak maximum at 124° C.)

The product obtained is characterized by a X-ray diffraction pattern obtained by using Cu—Kα-radiation which exhibits the diffraction angles (2-Theta):

| 2-Theta | Counts per second |
|---|---|
| 3.49 | 137 |
| 6.67 | 5421 |
| 6.99 | 3946 |
| 7.41 | 2659 |
| 8.91 | 33 |
| 9.61 | 86 |
| 10.47 | 149 |
| 11.49 | 353 |
| 12.29 | 468 |
| 13.29 | 284 |
| 14.54 | 461 |
| 15.68 | 317 |
| 16.21 | 47 |
| 17.52 | 652 |
| 17.91 | 827 |
| 19.14 | 730 |
| 20.88 | 321 |
| 22.00 | 211 |
| 22.49 | 309 |
| 24.03 | 54 |
| 24.88 | 272 |
| 25.67 | 360 |
| 26.28 | 189 |

Methods:

I) Differential Scanning Calorimetry (DSC):

A Perkin-Elmer DSC Instrument® (Model: DSC 820 FRS5), operated in a dry nitrogen atmosphere, is used for the analysis of the crystallization behavior of the product, according to standard procedures. About 5 to 10 mg of sample is sealed into an aluminum cup, heated from 30° C. to 180° C. at a rate of 10° C./min, and then subsequently cooled at a rate of 10° C./min to 0° C.

II) X-Ray Diffraction Pattern Obtained by Cu—Kα-Radiation:

Measuring equipment: X-ray diffractometer D 500 (independent theta/2-theta drives)

Manufacturer: BRUKER AXS (formerly SIEMENS-ALBIS)

X-ray generator: Kristalloflex K 710H (max. 2.7 kW, 20-55 kV, 5-60 mA)

Control device: Daco-MP

Detector: Scintillation counter

X-ray tube: Type FK60-04 with copper anode 40 samples changer

Measurement Setup:

The powder sample is placed in a specimen carrier in the middle between the Cu X-ray radiation source (α-radiation: kα1, λ=1.540598 Å, kα2, λ=1.544426 Å) and the detector.

The specimen is gradually rotated with constant angular speed, whereas the detector moves about the specimen at double the angular speed (θ/2θ coupled).

The diffraction angle (2θ) is thus always equal to double the glancing angle (θ).

kβ reflections are suppressed by means of a filter.

Focusing is accomplished according to Bragg-Brentano "tube-divergence diaphragm-specimen-convergence diaphragm-detector diaphragm-detector" using two divergence diaphragms (aperture diaphragm I=1.0°, aperture diaphragm II=1.0°, a convergence diaphragm (aperture diaphragm III=0.3°, a kβ filter and a detector diaphragm (0.018°.

The sample is positioned in a way that the optical path (X-ray radiation-specimen-X-ray diffraction) is retained parallel to the goniometer (χ=0°).

For averaging particle size distribution and texture the powder samples are rotating continuously round the perpendicular to their surface (Φ=0 . . . 360°).

The diffractograms measured from 2θ=3-43° are recorded in increments of 2θ=0.02° (dwell time=2 s).

Likewise of particular interest is the use of the present crystalline form as stabilizer in the applications described in US-A-2006/0,252,857, APPLICATION EXAMPLES, [0391] to [0400] and US-A-2006/0,052,491, EXAMPLES 1 to 24 for a similar UV stabilizer (system).

The disclosures of US-A-2006/0,252,857 and US-A-2006/0,052,491 are incorporated herein by reference.

EXAMPLE 1

Stabilization of a Polycarbonate (PC) Injection Molding Sample

Grinded polycarbonate (Lexan 145®, manufactured by GE Innovation Polymer) is dried in a vacuum drier (Vacutherm 1400®) for 6 hours at 120° C. and mixed with the product of Example A in an inner mixer (MTI/M20 FU) at 80° C. The mixture is compounded at 280° C. with a twin-screw extruder (Berstorff ZE 25×32D®). After drying of the composition obtained for 6 hours at 120° C., 2 mm plates of the compounded materials are prepared by an injection molding machine (Arburg 320 S®), the barrel temperature being 300° C.

Accelerated weathering is performed using an Atlas Ci65A® Weather-O-meter (=WOM), operated in dry mode (ASTM G 26 A).

The haze is measured with a Haze-Gard Plus® (BYK Gardner®) according to ASTM D-1003.

The results are listed in Table 1.

TABLE 1

| UV Stabilizer | Haze*) after dry weathering time in h | | | |
|---|---|---|---|---|
| | 0 | 257 h | 497 h | 1000 h |
| None | 2.4 | 2.9 | 4.6 | 6.6 |
| 0.3% of the product of Example A | 1.2 | 1.6 | 1.9 | 2.1 |

*)Low values are desired.

EXAMPLE 2

Stabilization of a Polymethyl Methacrylate (PMMA) Film Sample 10 g of polymethyl methacrylate (Plexiglas 7N, manufactured by Evonik) is solved in 40 g of dichloromethane with the product of Example A at room temperature. 5 g of this solution is poured on a crystal plate and the solution is equally spread on the crystal plate by an Erichen® casting machine at room temperature. After 10 minutes evaporation of the solvent, a 20 micron solution cast film is prepared.

Accelerated weathering is performed using an Atlas Ci65A® Weather-O-meter (=WOM), operated in dry mode (ASTM G 26 C).

The haze is measured with a Haze-Gard® plus (BYK Gardner®) according to ASTM D-1003.

The results are listed in Table 2.

TABLE 2

| UV Stabilizer | Haze*) after dry weathering time in h | | | | |
|---|---|---|---|---|---|
| | 0 | 999 | 1998 | 2998 | 3966 |
| None | 0.3 | 0.5 | 0.8 | 1.1 | 1.3 |
| 1% of the product of Example A | 0.3 | 0.4 | 0.6 | 0.6 | 0.6 |

*)Low values are desired.

EXAMPLE 3

Concentration of UV Stabilizer after Extrusion with Polycarbonate (PC)

Grinded polycarbonate (Makrolon 3108 FBL®, manufactured by Bayer Material Science) is dried in a vacuum drier (Vacutherm 1400®) for 6 hours at 120° C. Then the dried polycarbonate powder and 5%, relative to the weight the polycarbonate, of the product of Example A are feeded by two different feeders to a twin-screw extruder (Berstorff ZE 25×32D®) and are compounded at 280° C. The compounded pellets are collected after regular interval and analyzed for the concentration of the product of Example A.

The results are listed in Table 3.

TABLE 3

Concentration of the product of Example A during compounding.

| Concentration after compounding time in min | | | | |
|---|---|---|---|---|
| 5 min | 10 min | 15 min | 30 min | 40 min |
| 5.21% | 5.25% | 5.21% | 5.03% | 4.78% |

The invention claimed is:

1. A crystalline form of 2-(4,6-bis-biphenyl-4-yl-1,3,5-triazin-2-yl)-5-(2-ethyl-(n)-hexyloxy)phenol, characterized by a X-ray diffraction pattern obtained by using Cu—Kα-radiation which exhibits the diffraction angles (2-Theta)

| 2-Theta | Counts per second |
|---|---|
| 3.49 | 137 |
| 6.67 | 5421 |
| 6.99 | 3946 |
| 7.41 | 2659 |
| 8.91 | 33 |
| 9.61 | 86 |
| 10.47 | 149 |
| 11.49 | 353 |
| 12.29 | 468 |
| 13.29 | 284 |
| 14.54 | 461 |
| 15.68 | 317 |
| 16.21 | 47 |
| 17.52 | 652 |
| 17.91 | 827 |
| 19.14 | 730 |
| 20.88 | 321 |
| 22.00 | 211 |
| 22.49 | 309 |
| 24.03 | 54 |
| 24.88 | 272 |
| 25.67 | 360 |
| 26.28 | 189. |

2. A process for the preparation of the crystalline form of 2-(4,6-bis-biphenyl-4-yl-1,3,5-triazin-2-yl)-5-(2-ethyl-(n)-hexyloxy)phenol according to claim 1, which process comprises reacting 4-(4,6-bis-biphenyl-4-yl-1,3,5-triazin-2-yl)-benzene-1,3-diol and 2-ethyl-(n)-hexylbromide in an aprotic polar organic solvent in the presence of a base;

removing the organic solvent and cooling the residual melt to a temperature of 80° C. to 130° C.;

adding a solvent (S) selected from the group consisting of linear or branched $C_4$-$C_{20}$alkane or the isomeric mixture thereof, and $C_6$-$C_{12}$cycloalkane unsubstituted or substituted by 1 to 3 $C_1$-$C_8$alkyl, or the isomeric mixture thereof;

cooling the mixture to a temperature of 50° C. to 90° C.;

washing with water to remove the salt formed during reaction; and crystallizing 2-(4,6-bis-biphenyl-4-yl-1,3,5-triazin-2-yl)-5-(2-ethyl-(n)-hexyloxy)phenol from the organic phase.

3. A method for stabilizing an organic material against degradation induced by light, heat and oxidation, which comprises incorporating therein the crystalline form of 2-(4,6-bis-biphenyl-4-yl-1,3,5-triazin-2-yl)-5-(2-ethyl-(n)-hexyloxy) phenol according to claim 1.

4. A stabilizer mixture containing the crystalline form of 2-(4,6-bis-biphenyl-4-yl-1,3,5-triazin-2-yl)-5-(2-ethyl-(n)-hexyloxy)phenol according to claim 1 and further one or more conventional additives for organic polymers.

5. A stabilizer mixture according to claim 4 wherein the conventional additives are selected from the group consisting of alkylated monophenols, alkylthiomethylphenols, hydroquinones, and alkylated hydroquinones, tocopherols, hydroxylated thiodiphenyl ethers, alkylidenebisphenols, O-, N- or S-benzyl compounds, hydroxybenzylated malonates, aromatic hydroxybenzyl compounds, triazine compounds, benzylphosphonates, acylaminophenols, esters of β-(3,5-di-tert-butyl-4-hydroxyphenyl)propionic acid with mono- or polyhydric alcohols, esters of β-(5-tert-butyl-4-hydroxy-3-methylphenyl)propionic acid with mono- or polyhydric alcohols, esters of β-(3,5-dicyclohexyl-4-hydroxyphenyl)propionic acid with mono- or polyhydric alcohols, esters of 3,5-di-tert-butyl-4-hydroxyphenyl acetic acid with mono- or polyhydric alcohols, amides of β-(3,5-di-tert-butyl-4-hydroxyphenyl)propionic acid, ascorbic acid, aminic antioxidants, 2-(2'-hydroxyphenyl)benzotriazoles, 2-hydroxybenzophenones, esters of substituted or unsubstituted benzoic acids, acrylates, nickel containing light stabilizers, sterically hindered amines, oxamides, further 2-(2-hydroxyphenyl)-1,3,5-triazines, metal deactivators, phosphites, phosphonites, hydroxylamines, nitrones, thiosynergists, peroxide scavengers, polyamide stabilizers, basic co-stabilizers, nucleating agents, fillers, reinforcing agents, plasticisers, lubricants, emulsifiers, pigments, rheology additives, catalysts, flow-control agents, optical brighteners, flameproofing agents, antistatic agents, blowing agents, benzofuranones and indolinones.

6. A stabilizer mixture according to claim 4 wherein the conventional additive is a sterically hindered amine compound containing a divalent group of the formula

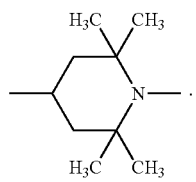

7. A stabilizer mixture according to claim 4 wherein the conventional additive is a further UV absorber.

8. A stabilizer mixture according to claim 4 wherein the conventional additive is an UV absorber selected from the group consisting of 2-(2'-hydroxyphenyl)benzotriazoles, 2-hydroxybenzophenones, 2-(2-hydroxyphenyl)-1,3,5-triazines and cyanoacrylate based UV absorbers; provided that the conventional additive is different from said crystalline form of 2-(4,6-bis-biphenyl-4-yl-1,3,5-triazin-2-yl)-5-(2-ethyl-(n)-hexyloxy)phenol.

9. A stabilizer mixture according to claim 4 wherein the conventional additive is a phosphite or phosphonite.

10. A composition containing an organic material subject to degradation induced by light, heat or oxidation and the crystalline form of 2-(4,6-bis-biphenyl-4-yl-1,3,5-triazin-2-yl)-5-(2-ethyl-(n)-hexyloxy)phenol according to claim 1.

11. A composition according to claim 10 wherein the organic material is a synthetic polymer.

12. A composition according to claim 10 wherein the organic material is a polyolefin.

13. A composition according to claim 10 wherein the organic material is an engineering plastic.

14. A composition according to claim 10 wherein the organic material is an acrylic, a polyester or a polycarbonate.

15. An article made of a composition containing an organic material subject to degradation induced by light, heat or oxidation and the crystalline form of 2-(4,6-bis-biphenyl-4-yl-1,3,5-triazin-2-yl)-5-(2-ethyl-(n)-hexyloxy)phenol according to claim 1.

16. An article according to claim 15 which is a molding, rotomolded article, injection molded article, blow molded article, film, tape, mono-filament, fiber, non-woven, profile, adhesive, putty or surface coating.

17. An article according to claim 15 which is an agricultural article.

18. An article according to claim 15 which is an agricultural article selected from the group consisting of mulch films, small tunnel films, banana bags, direct covers, non-woven, twines and pots.

19. An article according to claim 15 which is a film, panel or multilayer sandwich panel and wherein the organic material is a polycarbonate, an acrylic or a polyester.

20. A crystalline form of 2-(4,6-bis-biphenyl-4-yl-1,3,5-triazin-2-yl)-5-(2-ethyl-(n)-hexyloxy)phenol characterized by a melting range of 118-126° C.

21. The crystalline form of 2-(4,6-bis-biphenyl-4-yl-1,3,5-triazin-2-yl)-5-(2-ethyl-(n)-hexyloxy)phenol according to claim 1 further characterized by a melting range of 118-126° C. with a peak maximum of 124° C.

* * * * *